United States Patent [19]

Pedersen et al.

[11] Patent Number: 5,763,406
[45] Date of Patent: Jun. 9, 1998

[54] METHOD FOR THE TREATMENT OF CONDITIONS CAUSED BY HERPES VIRUS INFECTIONS

[75] Inventors: Ove Pedersen, Bagsværd, Denmark; D. K. MacFadden, Toronto, Canada

[73] Assignee: Carlbiotech, Ltd. A/S, Copenhagen, Denmark

[21] Appl. No.: 481,840

[22] Filed: Jun. 7, 1995

Related U.S. Application Data

[63] Continuation of Ser. No. 107,777, filed as PCT/DK92/00053 Feb. 24, 1992, abandoned.

[30] Foreign Application Priority Data

Feb. 25, 1991 [DK] Denmark ................................. 0319/91

[51] Int. Cl.$^6$ .......................... A61K 38/08; A61K 38/00; A61K 38/12
[52] U.S. Cl. ..................... 514/16; 514/17; 514/18; 514/9; 530/328; 530/329; 530/330; 530/317
[58] Field of Search ............................... 530/328, 330; 514/17, 16

[56] References Cited

FOREIGN PATENT DOCUMENTS

| | | |
|---|---|---|
| 179412 | 10/1985 | European Pat. Off. . |
| 226158 | 12/1986 | European Pat. Off. . |
| 0249394 | 6/1987 | European Pat. Off. . |
| 249390 | 6/1987 | European Pat. Off. . |
| 2228937 | 3/1990 | United Kingdom . |
| 86/01211 | 8/1984 | WIPO . |
| 88/09338 | 5/1988 | WIPO . |
| 89/12067 | 5/1989 | WIPO . |
| 90/06946 | 12/1989 | WIPO . |

OTHER PUBLICATIONS

Pert, C. B. Small peptides which inhibit binding to T4 receptors on human T–lymphocytes, inhibition of AIDS virus infection by the peptides, and their use as immunogens. Chem. Abstracts #93418, 1989.

Identification of a Putative Cell Receptor for Human Cytomegalovirus, Adlish et al., Virology 176, 337–345 (1990).

New Methods and Reagents in Organic Synthesis. 55.+ 1 Total Synthesis of Patellamides B and C, Cytotoxic Cyclic Peptides From a Tunicate 1. Their Proposed Structures Should Be Corrected.2, Hamada, et al., Tetrahedron Letters, vol. 26, No. 42, pp. 5155–5158, 1985.

Prodrug derivatives of thyrotropin–releasing hormone and other peptides, Bundgaard, et al., Peptide Drug Delivery, vol. 17, 947–949, (1989).

*Primary Examiner*—Cecilia J. Tsang
*Assistant Examiner*—Michael Borin
*Attorney, Agent, or Firm*—Banner & Witcoff, Ltd.

[57] ABSTRACT

Peptides of the general formula (I): I-A-B-C-D-E-F-G-H-II are disclosed as being active against Herpes virus infections in animals and human beings, wherein A is Ala, Gly, Val or absent; B is Ala, Gly, Val, Ser or absent; C is Ser, Thr or absent; D is Ser, Thr, Ans, Glu, Arg, Ile, Leu or absent; E is Ser, Thr, Asp or absent; F is Thr, Ser, Asn, Gln, Lys, Trp or absent; G is Tyr or absent; H is Thr, Gly, Met, Met(O), Cys, Thr or Gly; I is Cys or absent, and II is Cys, an amide group, substituted amide group, an ester group or absent, wherein the peptides comprise at least 4 amino acids and physiologically acceptable salts thereof.

10 Claims, No Drawings

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
      ( A ) LENGTH: 8 amino acids
      ( B ) TYPE: amino acid
      ( C ) STRANDEDNESS:
      ( D ) TOPOLOGY: Linear ( i i ) MOLECULE TYPE: peptide ( x i ) SEQUENCE DESCRIPTION: SEQ ID NO:1:

Ala  Ser  Thr  Thr  Thr  Asn  Tyr  Thr
   1                       5

( 2 ) INFORMATION FOR SEQ ID NO:2:

( i ) SEQUENCE CHARACTERISTICS:
      ( A ) LENGTH: 8 amino acids
      ( B ) TYPE: amino acid
      ( C ) STRANDEDNESS:
      ( D ) TOPOLOGY: Linear ( i i ) MOLECULE TYPE: peptide ( x i ) SEQUENCE DESCRIPTION: SEQ ID NO:2:

Ala  Ser  Thr  Thr  Thr  Asn  Tyr  Thr
   1                       5

( 2 ) INFORMATION FOR SEQ ID NO:3:

( i ) SEQUENCE CHARACTERISTICS:
      ( A ) LENGTH: 8 amino acids
      ( B ) TYPE: amino acid
      ( C ) STRANDEDNESS:
      ( D ) TOPOLOGY: Linear ( i i ) MOLECULE TYPE: peptide ( x i ) SEQUENCE DESCRIPTION: SEQ ID NO:3:

Ala  Ser  Thr  Thr  Thr  Asn  Tyr  Thr
   1                       5

( 2 ) INFORMATION FOR SEQ ID NO:4:

( i ) SEQUENCE CHARACTERISTICS:
      ( A ) LENGTH: 8 amino acids
      ( B ) TYPE: amino acid
      ( C ) STRANDEDNESS:
      ( D ) TOPOLOGY: Linear ( i i ) MOLECULE TYPE: peptide ( x i ) SEQUENCE DESCRIPTION: SEQ ID NO:4:

Ala  Ala  Ser  Ser  Ser  Asn  Tyr  Met
   1                       5

( 2 ) INFORMATION FOR SEQ ID NO:5:

( i ) SEQUENCE CHARACTERISTICS:
      ( A ) LENGTH: 5 amino acids
      ( B ) TYPE: amino acid
      ( C ) STRANDEDNESS:
      ( D ) TOPOLOGY: Linear -continued (ii) MOLECULE TYPE: peptide (xi) SEQUENCE DESCRIPTION: SEQ ID NO:5:

Thr Asp Asn Tyr Thr
1               5

(2) INFORMATION FOR SEQ ID NO:6:

(i) SEQUENCE CHARACTERISTICS:
  (A) LENGTH: 5 amino acids
  (B) TYPE: amino acid
  (C) STRANDEDNESS:
  (D) TOPOLOGY: Linear (ii) MOLECULE TYPE: peptide (xi) SEQUENCE DESCRIPTION: SEQ ID NO:6:

Thr Thr Ser Tyr Thr
1               5

(2) INFORMATION FOR SEQ ID NO:7:

(i) SEQUENCE CHARACTERISTICS:
  (A) LENGTH: 5 amino acids
  (B) TYPE: amino acid
  (C) STRANDEDNESS:
  (D) TOPOLOGY: Linear (ii) MOLECULE TYPE: peptide (xi) SEQUENCE DESCRIPTION: SEQ ID NO:7:

Thr Thr Asn Tyr Thr
1               5

METHOD FOR THE TREATMENT OF CONDITIONS CAUSED BY HERPES VIRUS INFECTIONS

This application is a continuation of application Ser. No. 08/107,777, filed as PCT/DK92/00053 Feb. 24, 1992 (abandoned).

BACKGROUND OF THE INVENTION

The present invention relates to peptides that are useful in the treatment of diseases or conditions caused by herpes viruses, such as Herpes Simplex Virus types 1 and 2, Varicella Zoster Virus, Epstein-Barr Virus and Cytomegalovirus. The peptides are also useful in the treatment of diseases or conditions caused by the family of herpes viruses in animals, such as for example Aujeszky's disease in pigs, bovine rhinotracheitis, rhinopharyngitis in horses, laryngotracheitis in poultry and Marek's disease in chickens. Further, the peptides can be used for diagnostical purposes.

Originally, most of the peptides of the invention have been described to be useful in the treatment of acquired immune deficiency syndrome (AIDS) and its related diseases, see EP 0 249 390, EP 0 249 394 and WO 88/09338, which are incorporated by reference. All compounds disclosed in these specifications are useful for the present invention. The original peptide has its basic point of origin in the octapeptide Ala-Ser-Thr-Thr-Thr-Asn-Tyr-Thr,[SEQ ID NO: 1] called Peptide T because 50% of the amino acid residues are threonines. This peptide has been identified from a subregion of the "human immune deficiency virus" (HIV) external glycoprotein molecule, gp120, responsible for binding to brain membrane and human lymphocytes, especially human T cells via the receptor CD4 on these cells. Treating individuals infected with HIV with this peptide and the derivatives to be described below, consequently has the effect of potentially inhibiting binding of gp120 to the cell receptor CD4. In this way, the cell is protected from infection, and the virus is left without any possibility of replicating and will sooner or later be destroyed by the immune defence.

DESCRIPTION OF THE PRIOR ART

Despite the theoretical basis for designing the peptide, we have surprisingly found the peptides to be effective in the treatment of Herpes Simplex Virus (HSV). Surprisingly because the peptides are specially constructed to fit into the CD4 receptor, which again is a special nomenclature for receptor for lymphocytes and hence the immune system. The primary target for HSV is not the cell types governing the immune system, but rather epithelial cells, fibroblast cells and nerve cells, and these types of cells are not believed to express the same receptors on the surface. Furthermore, the HIV and HSV are in principle totally different in mode of action and composition. HSV belongs to the "normal" group of viruses, while HIV belongs to the class of retroviruses. A retrovirus, when infecting a cell, is liberating RNA into the cell. The RNA is transcribed into the form of DNA in order to become incorporated as a permanent part of the host cell genome. This can be done because the retroviruses themselves contain "RNA-directed DNA polymerase", also called "reverse transcriptase". Once this step has taken place, the normal route of viral synthesis takes place. The "normal" viruses contain DNA and do not need a "reverse transcriptase".

There are various known peptide compounds some of which have a pharmaceutical effect of a different type, see e.g. WO 89/12067, GB 2228937, WO 86/01211, WO 90/06946 and Chem. Pharm. Bull. 31(1983):7.

EP 266 158 discloses peptides derived from lysozyme, said peptides allegedly inhibit herpetic infections, however, they differ considerably in structure from the peptides according to the present invention.

It is well known that quite a few drugs are being tested and/or used for treatment of both categories of viruses, but these drugs are typically compounds that interfere with the synthetic mechanisms inside an infected cell.

As examples can be mentioned aciclovir, which today is the preferred drug for treatment of HSV infections, and Zidovudin, which today is the only treatment for the retrovirus HIV. Both are derivatives of a nucleotide and both interfere with the synthetic mechanism that takes place within the cell.

Aciclovir is a derivative of deoxoyguanosine, in which the cyclic deoxyribose unit is replaced by a linear chain. The compound works selectively on HSV infected cells in two different ways. At first the HSV specific thymidine kinase will convert aciclovir into aciclovir monophosphate which will mainly stay inside the infected cell where an upconcentration of aciclovir is taking place. Secondly, aciclovir monophosphate is converted into the active aciclovir triphosphate compound which is an inhibitor of HSV-specific DNA-polymerase and is also incorporated into viral DNA, and consequently production of viruses stops. The drawback of the drug is that HSV develops resistance to aciclovir due to the selection of mutants deficient in thymidine kinase.

Zidovudin is a derivative of thymidine where one of the hydroxyl groups in the sugar chain is substituted by an azide group. It acts as an inhibitor of reverse transcriptase, thereby slowing down the production of viruses. The drawback of Zidovudin is the lack of specificity, which causes serious adverse effects.

Other candidates derived from nucleotides for the treatment of HSV comprise e.g. Bromovinyldeoxyuridine, Edoxudine, Fluoroiodoaracytosine, Ganciclovir, Ibacitabene, Idoxuridine, Inosine, Pranobex and Vidarabine. An early compound that is believed to act as a receptor blocker for penetration is Tromantadine, but quite often adverse effects like contact dermatitis have been reported. Tromantadine is neither derived from the nucleotide nor is it derived from a peptidic character, but is a derivative of Amantadine.

The peptides described in this invention have never been reported to penetrate any type of cells, but only to occupy the CD4 receptors found on lymphocytes. The chemical nature as well as the mode of action are very different from the compounds described above and novel for the treatment of HSV.

Another advantage related to the peptides is connected with the relative easiness by which they apparently penetrate the skin. The peptides are predominantly hydrophilic by nature and common practice dictates that drugs intended to be transported transdermally should be hydrophobic by nature, see H. Bundgaard, and J. M+e,sez o+ee ss, Biochem. Soc. Trans., 5, p. 947–949, 1989.

A major advantage of the peptides is their almost complete lack of toxicity, which again means that the use of high doses for an extended period of time is possible without any drawbacks (Hesseltine, P., et al, Sixth Int. Conf. on AIDS, San Francisco, Calif., USA, 20–24 Jun. 1990).

DESCRIPTION OF THE INVENTION

The present invention relates to linear or cyclic peptides of the general formula:

I-A-B-C-D-E-F-G-H-II          I wherein A is Ala, Gly, Val or absent,
B is Ala, Gly, Val , Ser or absent,
C is Ser, Thr or absent,
D is Ser, Thr, Asn, Glu, Arg, Ile, Leu or absent,
E is Ser, Thr, Asp or absent,
F is Thr, Ser, Asn, Gln, Lys, Trp or absent,
G is Tyr or absent,
H is Thr, Gly, Met, Met(O), Cys, Thr, or Gly
I is Cys or absent,
II is Cys or absent,
or a pharmaceutically acceptable salt thereof.

All of the mentioned amino acids may be in the configuration of L- or D-isomers, and candidates for H might be esterified or amidated. The peptide comprises at least 4 amino acids.

The tetra-, penta-, hexa-, hepta-, octa- and nonapeptides are all of the peptides chosen within the sequence:

I-A-B-C-D-E-F-G-H-II by deleting one at a time from either the carboxyl or amino terminal.

Most preferred peptides are the following:
1. D-Ala-Ser-Thr-Thr-Thr-Asn-Tyr-Thr-NH$_2$ [SEQ ID NO: 2]
2. Ala-Ser-Thr-Thr-Thr-Asn-Tyr-Thr [SEQ ID NO: 1]
3. D-Ala-Ser-Thr-Thr-Thr-Asn-Tyr-Thr [SEQ ID NO: 3]
4. D-Ala-Ala-Ser-Ser-Ser-Asn-Tyr-Met [SEQ ID NO: 4]
5. Thr-Asp-Asn-Tyr-Thr [SEQ ID NO: 5]
6. Thr-Thr-Ser-Tyr-Thr [SEQ ID NO: 6]
7. Thr-Thr-Asn-Tyr-Thr [SEQ ID NO: 7]

Quite often it may be an advantage to have the amino terminal amino acid as a D-stereoisomer, to protect the molecule from degradation from aminopeptidases, and the carboxy terminal amino acid may also quite often be an amino acid amide to protect the molecule from degradation from carboxypeptidases.

Compounds 5, 6 and 7 include the analogues with D-Thr as the amino terminal residue and/or an amide derivative at the carboxy terminal.

Furthermore, it should be understood that one or more of the amino acids in the peptides may be substituted N-alkyl amino acids instead of primary amino acids, e.g. substituted by methyl or ethyl. The hydroxyl group side chains of one or more of the amino acids (Ser, Thr, Tyr) may be derivatized into an ether or ester group. Any alkyl ester or ether may be formed, for example phenylester, benzylether or thiophenol ethylester. The presently preferred ethers are methyl, ethyl and propylethers, and presently preferred esters are methyl, ethyl and propylester.

The linear peptides described in this invention may be prepared by any process, such as conventional solid phase peptide synthetic techniques, see Solid Phase Peptide Synthesis, 2nd ed., J. M. Stewart, J. D. Young, Pierce Chemical Company, 1984, ISBN: 0-935940-03-0. Another possibility is solution phase techniques.

The cyclic peptides may be prepared by known techniques, such as, for example, described in Y. Hamada, Tetrahedron Letters, vol. 26, p. 5155, 1985.

The cyclic peptides may be established in the form of an -S-S- bridge between two Cys-residues and/or reacting the carboxy terminal amino acid residue with the amino terminal residue and/or reacting the amino terminal residue with for example the gamma carboxyl group of Glu, when Glu is at position D.

The invention also relates to pharmaceutical compositions and compositions of matter comprising the peptides for treating or preventing any disease or condition caused by Herpes viruses, especially Herpes Simplex Virus-1 (HSV-1), Herpes Simplex Virus-2 (HSV-2), Varizella Zoster Virus (VZV), Human Cytomegalovirus (HCV) or Epstein-Barr Virus (EBV).

The peptides can be used for the manufacture of a medicament for treatment of or preventing any disease or condition caused by Herpes viruses, especially Herpes Simplex Virus-1 (HSV-1), Herpes Simplex Virus-2 (HSV-2), Varizella Zoster Virus (VZV), Human Cytomegalovirus (HCV) or Epstein-Barr Virus (EBV).

The peptides and the compositions according to the invention may be administered orally, buccally, parenterally, topically, rectally or by inhalation spray.

In particular, the peptides according to the invention may be formulated for topical use, for inhalation by spray, for injection or for infusion and may be presented in unit dose form in ampoules or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, e.g. sterile, pyrogen-free water, before use.

The pharmaceutical compositions according to the invention may also contain other active ingredients such as anti-microbial agents, or preservatives.

The compositions may contain from 0.001–99% of the active ingredient.

The compositions are administered in therapeutically or immunogenically effective doses, i.e. 0.05–10000 mg of peptide per day, preferred 0.5–1000 mg of peptide per day, in particular 5–100 mg per day. Very large doses may be used as the peptide according to the invention is non-toxic. However, normally this is not required. The dose daily administered of course depends on the disease or condition to be treated or prevented and on the mode of administering.

The invention further provides a method for treatment of any illness caused by Herpes Simplex Virus-1 (HSV-1), Herpes Simplex Virus-2 (HSV-2), Varizella Zoster Virus (VZV), Human Cytomehalovirus (HCV) or Epstein-Barr Virus (EBV), wherein a peptide or a composition is administered in an effective amount for treatment of the illness caused by the virus.

All usual excipients and carriers can be used in the composition of the invention.

It will of course also be possible to use the peptides of this invention for diagnoses of Herpes viruses.

Experimental data

Example 1

A 38-year-old Caucasian male with a two-day history of painful lesions of the lower lip, clinically consistent with HSV-1 infection, was examined.

The patient had experienced similar lesions during the past 18 years, primarily during the winter months. He would usually experience 3–5 outbreaks each winter lasting 10–14 days before complete resolution. One year ago, he applied aciclovir topical to the lesions and on that occasion, resolution occured in 6–8 days.

On this occasion, he denied recent use of any topical or systemic therapy.

On examination, he appeared as a well man, afibrile and vital signs within normal limits.

There were two immature vesicles, one mature vesicle, two vesicles that had already ulcerated and a small patch of skin that was erythematous and painful to palpation, indicating a site of future vesicle formation. In addition, there were two three mm diameter ulcers on the buccal surface of the lower lip. No significant adenopathy was palpable at any site.

The patient was given (D-Ala$^1$)-Peptide-T Amide, 10 mg/ml in pyrogen-free distilled water to be applied to the lesions as a thin film three times daily. Within 36 hours, the early lesions as well as the vesicular lesions had virtually resolved and the ulcerative lesions were healing well. Essentially, complete resolution was achieved within 3 days and within 6 days the ulcerated lesions had cleared. No drug was applied to the lesions of the buccal mucosa, however they had also resolved within 4 days.

The patient did not report any systemic or local effects other than those noted above.

No other medications were used concomitantly.

Example 2

A 42-year-old Caucasian female with a one-day history of a painful lesion just under the right nostril, consistent clinically with HSV-1 infection, was examined. The patient had experienced lesions caused by HSV-1 regularly during the last three years, normally in connection with a cold. Normal frequency of outbreaks would be 6–7 times per year, lasting approximately 12–14 days before a complete resolution. The outbreaks would normally be centered around the nostrils and on the lips and would, untreated, develop into open and painful suppurating ulcers with a diameter close to 8 mm.

When the lesions are treated with a 5% aciclovir ointment, topically, resolution is normally achieved within 6–7 days. Very early treatment of the lesions with aciclovir has not been able to stop the vesicles developing into painful ulcers although the ulcers tend to decrease in size. On this occasion, she denied any recent use of any topical or systemic therapy.

There was one mature painful vesicle situated just under the right nostril. The patient was given (D-Ala$^1$)-Peptide-T Amide, 10 mg/ml in pyrogen-free distilled water to be applied three times per day. Immediately after the first treatment, the patient experienced a relief of pain and after two days, resolution had occured without the vesicles developing into open ulcers.

Example 3

The same patient as described in example 2 was, four weeks later, treated for a new attack of HSV-1. Four mature one-day old painful vesicles had developed. They were treated with (D-Ala$^1$)-Peptide-T Amide, 2 mg/ml in pyrogen-free distilled water. The drug was applied in a thin film twice a day for two days and the outcome was a repeating of the first treatment described in example two. The vesicles were resolved without developing into ulcers.

However, the vesicles were appearing again one day after the treatment had stopped and the same solution of the drug was applied for the next two days, twice a day, with complete resolution of the vesicles. No outburst was observed within the next month.

Example 4

A 29-year-old Caucasian male with a 2-day history of ulcerated lesions in the left nostril, consistent clinically with HSV-1 infection, was examined. The patient had experienced lesions caused by HSV-1 regularly during the last 10 years with a frequency of 3–5 times per year. Untreated, the lesions would normally have healed within 12–15 days. The outbreaks would normally be centered just inside the nostrils and under the nose.

The patient has never experienced any effect from the use of aciclovir.

The ulcer was treated with (D-Ala$^1$)-Peptide-T Amide, 10 mg/ml in water, four times in 36 hours. Within 48 hours, the ulcers had become dry and then disappeared. No medications were used concomitantly and the patient did not experience any systemic or local effects other than those noted above.

Example 5

A 23-year-old Caucasian female with a thirteen-day history of painful lesions of the upper lip, consistent clinically with HSV-1 infection, was examined.

The patient had experienced outbreaks from HSV-1 from the age of two. Five years ago the patient started to use aciclovir topically on a regular basis, but switched to take aciclovir orally 1½ years ago. Normally the outbreaks would be on the lips, but occasionally the outbreaks would also appear on the neck and on the buccal mucosa. Without any form of medication, complete resolution would happen within 2–3 weeks and complete resolution by using aciclovir orally would happen within 1–2 weeks.

On this occation, the patient had started treatment of a HSV-1 outbreak on the left side of the upper lip by aciclovir tablets (200 mg per tablet, 3–5 tablets per day), just as the first outbreak appeared 11 days ago and before mature vesicles had appeared. The treatment continued for five days until ulceration had occured. Five days later, another outbreak started approximately 0.5 cm away from the first outbreak, which was still ulcerated. No treatment by any medication was started this time and within the next three days, several small vesicles were developing into one large vesicle followed by ulceration that easily cracked causing pain.

The patient was given (D-Ala$^1$)-Peptide-T Amide,. 10 mg/ml in pyrogen-free destined water, to be applied to the lesion two times daily as a thin film. An immediate decrease in the size of the vesicle and the ulcer was observed, and within seven days complete resolution had occured.

Compared to the aciclovir treatment, the following differences were observed: The ulcer was thinner and did not tend to crack and bleed as easily as usually and the pain related to the outbreak from the time of ulceration was heavily reduced compared with treatment using aciclovir.

The patient did not observe any systemic or local effects other than those noted above.

We claim:

1. A method of treating a condition caused by a Herpes virus selected from the group consisting of Herpes Simplex Virus-1 (HSV-1), Herpes Simplex Virus-2 (HSV-2), and Varizella Zoster Virus (VSV), the method comprising administering to a subject a therapeutically effective amount of a linear or cyclic peptide of the general formula:

I-A-B-C-D-E-F-G-H-II or a physiologically acceptable salt thereof,
  wherein A is Ala, Gly, Val, or absent,
  B is Ala, Gly, Val, Ser or absent,
  C is Ser, Thr or absent,
  D is Ser, Thr, Asn, Glu, Arg, Ile, Leu or absent,
  E is Ser, Thr, Asp or absent,
  F is Thr, Ser, Asn, Gln, Lys, Trp or absent,
  G is Tyr or absent,
  H is Thr, Gly, Met, Met (O) or Cys,
  I is Cys or absent, and
  II is Cys, an amide group, substituted amide group, an ester group or absent, wherein the peptide comprises at least 4 amino acids and wherein the amino acids, except Gly, are L- or D-stereoisomers.

2. A method as claimed in claim 1, wherein the peptide is conjugated to a protein or another appropriate carrier and/or excipient.

3. A method as claimed in claim 1, wherein the peptide is a tetra-, penta-, hexa-, hepta-, octa-, or nonapeptide, where one or more amino acids are deleted from either the carboxy or amino terminal, and where the carboxy terminal amino acid can be in the form of an amide, substituted amide or an ester.

4. A method as claimed in claim 3, wherein at least one of the hydroxyl groups on a Ser, Thr or Tyr in the peptide is derivatized into an ester or ether compound.

5. A method as claimed in claim 3, wherein at least one of the amino acids in the peptide is a substituted N-alkyl amino acid.

6. A method as claimed in claim 1, wherein the peptide is selected from the group consisting of:

D-Ala-Ser-Thr-Thr-Thr-Asn-Tyr-Thr-NH$_2$[SEQ ID NO: 2];

Ala-Ser-Thr-Thr-Thr-Asn-Tyr-Thr [SEQ ID NO: 1];

D-Ala-Ser-Thr-Thr-Thr-Asn-Tyr-Thr [SEQ ID NO: 3];

D-Ala-Ala-Ser-Ser-Ser-Asn-Tyr-Met [SEQ ID NO: 4];

Thr-Asp-Asn-Tyr-Thr [SEQ ID NO: 5];

Thr-Thr-Ser-Tyr-Thr [SEQ ID NO: 6]; and

Thr-Thr-Asn-Tyr-Thr [SEQ ID NO: 7]

or a derivative or salt thereof.

7. A method as claimed in claim 1, wherein the peptide is D-Ala-Ser-Thr-Thr-Thr-Asn-Tyr-Thr-NH$_2$[SEQ ID NO:2].

8. A method as claimed in claim 1, wherein the therapeutically effective amount comprises about 0.05 mg to about 10000 mg of peptide per day.

9. A method as claimed in claim 1, wherein the therapeutically effective amount comprises about 0.5 mg to about 1000 mg of peptide per day.

10. A method as claimed in claim 1, wherein the therapeutically effective amount comprises about 5 mg to about 100 mg of peptide per day.

* * * * *